US00PP20817P2

(12) United States Plant Patent
de Looff

(10) Patent No.: US PP20,817 P2
(45) Date of Patent: Mar. 9, 2010

(54) ***LILIUM* PLANT NAMED 'DOUBLE STAR'**
(50) Latin Name: *Lilium hybrida*
Varietal Denomination: Double Star

(75) Inventor: Tonny M. de Looff, Koudekerke (NL)

(73) Assignee: DeLooff Lily Innovation BV., Kouderkerk (NL)

( * ) Notice: Subject to any disclaimer, the term of this patent is extended or adjusted under 35 U.S.C. 154(b) by 0 days.

(21) Appl. No.: 12/317,888

(22) Filed: Dec. 30, 2008

(51) Int. Cl.
*A01H 5/00* (2006.01)

(52) U.S. Cl. ..... Plt./315
(58) Field of Classification Search ..... Plt./315
See application file for complete search history.

*Primary Examiner*—Annette H Para
(74) *Attorney, Agent, or Firm*—Penny J. Aguirre

(57) ABSTRACT

A new cultivar of *Lilium hybrida* named 'Double Star', characterized by its double flowers that are pink in color, with petals that have deep pink midribs and lighter pink margins and it's flowers that lack functional reproductive organs and pollen.

1 Drawing Sheet

Botanical classification: *Lilium hybrida.*
Varietal denomination: 'Double Star'.

BACKGROUND OF THE INVENTION

The present invention relates to a new and distinct cultivar of *Lilium hybrida* and will be referred to hereafter by its cultivar name, 'Double Star'. 'Double Star' represents a new Oriental lily, grown for use as a cut flower.

The new cultivar, 'Double Beauty' arose from an ongoing breeding program conducted by the Inventor in a greenhouse in Koudekerke, The Netherlands. 'Double Star' was selected in summer of 2001 as a single unique plant that arose from a cross made in summer of 1997 with an unnamed proprietary seedling as the female parent and *Lilium* 'Tiber' (U.S. Plant Pat. No. 16,900) as the male parent.

Asexual reproduction of the new cultivar was first accomplished by *in vitro* propagation under the direction of the Inventor in Heerhugowaard, The Netherlands in summer of 2002. It has been determined that the characteristics of the new cultivar are stable and are reproduced true to type in successive generations.

SUMMARY OF THE INVENTION

The following traits have been repeatedly observed and represent the characteristics of the new cultivar after observing plants grown outdoors in a field for five years in Koudekerke, The Netherlands. These attributes in combination distinguish 'Double Star' as unique from all other varieties of Oriental lilies known to the Inventor.

1. 'Double Star' exhibits double flowers.
2. 'Double Star' exhibits flowers with petals that are pink in color with deep pink midribs with lighter pink margins.
3. 'Double Star' produces flowers that lack functional reproductive organs and pollen.

'Double Star' differs from its female parent plant in having a greater number of petaloids. 'Double Star' differs from its male parent, 'Tiber' in having double flowers whereas 'Tiber' exhibits single flowers. The Inventor is familiar with many commercial cultivars and knows of no other cultivars that are similar in comparison to 'Double Star'. 'Double Star' can be compared to 'Miss Lucy' (U.S. Plant Pat. No. 15,916), another double flowering Oriental lily. 'Miss Lucy' differs in having flowers that are lighter pink in color and lacks the dark pink midribs.

BRIEF DESCRIPTION OF THE PHOTOGRAPHS

The plants and plant parts in the photographs were taken of plants of 'Double Star' as grown in a nursery bed in a greenhouse for 3 months from a bulb 4.5 cm in diameter (2.5 years in age) in Koudekerke, The Netherlands.

The photograph on the top of the sheet provides a close-up view of a flower and flower buds of 'Double Star'.

The photograph on the bottom of the sheet provides a close-up view of a leaf of 'Double Star'.

The colors in the photograph may differ slightly from the color values cited in the detailed botanical description, which accurately describe the colors of the new Oriental lily.

DETAILED BOTANICAL DESCRIPTION

The following is a detailed description of plants of 'Double Star' as grown in a nursery bed in a greenhouse for 3 months from a bulb 4.5 cm in diameter in Koudekerke, The Netherlands. Plants were grown under natural light with average day temperatures ranging from 15° to 30° C. and average night temperatures ranging from 12° to 17° C. The phenotype of the new cultivar may vary with variations in environmental, climatic, and cultural conditions, as it has not been tested under all possible environmental conditions. The color determination is in accordance with the 2001 R.H.S Colour Chart of The Royal Horticultural Society, London, England, except where general color terms of ordinary dictionary significance are used.

General description:

*Blooming period.*—June in The Netherlands.

*Plant type.*—Perennial bulb, grown for cut flower production.

*Plant habit.*—Upright.

*Height and spread.*—Average of 97.3 cm in height and 32.2 cm in spread.

*Cold hardiness.*—At least to U.S.D.A. Zone 5.

*Heat tolerance.*—At least to 40° C.

*Diseases and pests.*—Not more susceptible than other *Lilium* varieties.

*Root description.*—True bulb, globular in shape with a pointed apex, an average of 4.5 cm in height and 4.4 cm in diameter, N155B in color, surface is scaly and dull.

Growth and propagation:

*Propagation.*—Tissue culture preferred, bulb scales also possible.

*Cropping time to bloom.*—About 2.5 years from a rooted transplant from tissue culture to production of flowering stems suitable for cutting.

*Growth rate.*—Moderate to high.

Stem description:

*Stem shape.*—Round.

*Stem color.*—144B.

*Stem size.*—Average of 68.4 cm in length, average of 7 mm in diameter.

*Stem surface.*—Moderately glossy, glabrous, with thin waxy layer 145A in color.

*Stem aspect.*—Upright, strong.

*Internode length.*—Average of 1.9 cm.

*No. of harvestable cut flower stems.*—1 per bulb.

Foliage description:

*Leaf shape.*—Lanceolate.

*Leaf division.*—Simple.

*Leaf base.*—Attenuate.

*Leaf apex.*—Acuminate.

*Leaf venation.*—Parallel, upper surface 146C in color, lower surface is 146B in color.

*Leaf margins.*—Entire.

*Leaf attachment.*—Petiolate.

*Leaf arrangement.*—Alternate.

*Leaf surface.*—Glabrous and smooth on upper and lower surface.

*Leaf color.*—Young and mature; upper surface 139A, lower surface 137B.

*Leaf number.*—Average of 36 per stem.

*Leaf size.*—Average of 15.7 cm in length and 4.1 cm in width.

*Petioles.*—Flattened, average of 1.6 cm in length and 6 mm in width, 146C in color on upper surface and 146A in color on lower surface.

*Foliage durability to stress.*—High.

Flower description:

*Inflorescence type.*—Double flowers arranged in simple terminal cyme.

*Inflorescence size.*—Average of 29.6 cm in height and 35.3 cm in width.

*Flower fragrance.*—Strong, sweet and pleasant; typical oriental Lilium hybrid scent.

*Inflorescence longevity.*—Average of 14 days on plant, persistent, 14 days as a cut flower.

*Flower bud description.*—Narrowly ovate in shape, average of 3.9 cm in diameter and 10.6 cm in length, color is 145C to 145B with base 176A to 176B.

*Flower quantity.*—Average of 4 per stem.

*Flower aspect.*—Held outward.

*Flower form.*—Double, rotate.

*Flower size.*—15.9 cm in depth and 23.8 cm in diameter.

*Rate of opening.*—Flowers open with the lowest flowers opening first.

*Pedicels.*—None.

*Peduncles.*—7.1 cm in length and 6 mm in diameter with an average angle to stem of 50°, 143B in color, strong strength.

*Petals.*—3, about 13 cm in length and 5.5 cm in width, narrowly ovate to lanceolate in shape and curved, margin is entire and wavy, apex is rounded, surface is smooth and slightly glossy, arrangement is rotate, near the base of upper surface there is an average of 30 glands; 0.5 mm in length and 59C in color, color when opening upper surface; 70D with margin N155A and base N155A with a central band 144A to 144B, color when fully open upper surface; 64D to 70C with margin N155A with a more intense central band 58B and base N155A with a central band 144A to 144B, color when opening lower surface; 157B, base 145D, margins N155B, color when fully open lower surface; N155B, base 145D, margins N155B, central band 62D.

*Petaloids.*—15, about 13.2 cm in length and 4.8 cm in width, narrowly ovate to lanceolate in shape and concave, margin is entire, surface is smooth and slightly glossy in appearance, color matches coloration of petals.

*Calyx form.*—Rotate in form, average of 5.7 cm in length and 23.8 cm in diameter.

*Sepals.*—3, average of 13.6 cm in length, 5.1 cm in width, narrow ovate to lanceolate in shape, arrangement is rotate, margin is entire, apex is rounded, base is cuneate, surface is smooth and slightly glossy, color of upper surface 63C with a more vivid central band 58B, margins N155A, base 144A to 144B. Color of lower surface of sepal N155B changing to 75B to 75C near the base, base 178A, with a central vein 146C.

Reproductive organs:

*Gynoecium.*—1, pistil strongly deformed, about 2.3 cm in length, stigma is club shaped and strongly deformed 148D in color, tinged 61B, style is about 2.2 cm in length 145A in color, ovary is 145C to 145D in color.

*Androecium.*—No stamens present.

*Seeds.*—None observed.

It is claimed:

1. A new and distinct cultivar of *Lilium* plant named 'Double Star' as herein illustrated and described.

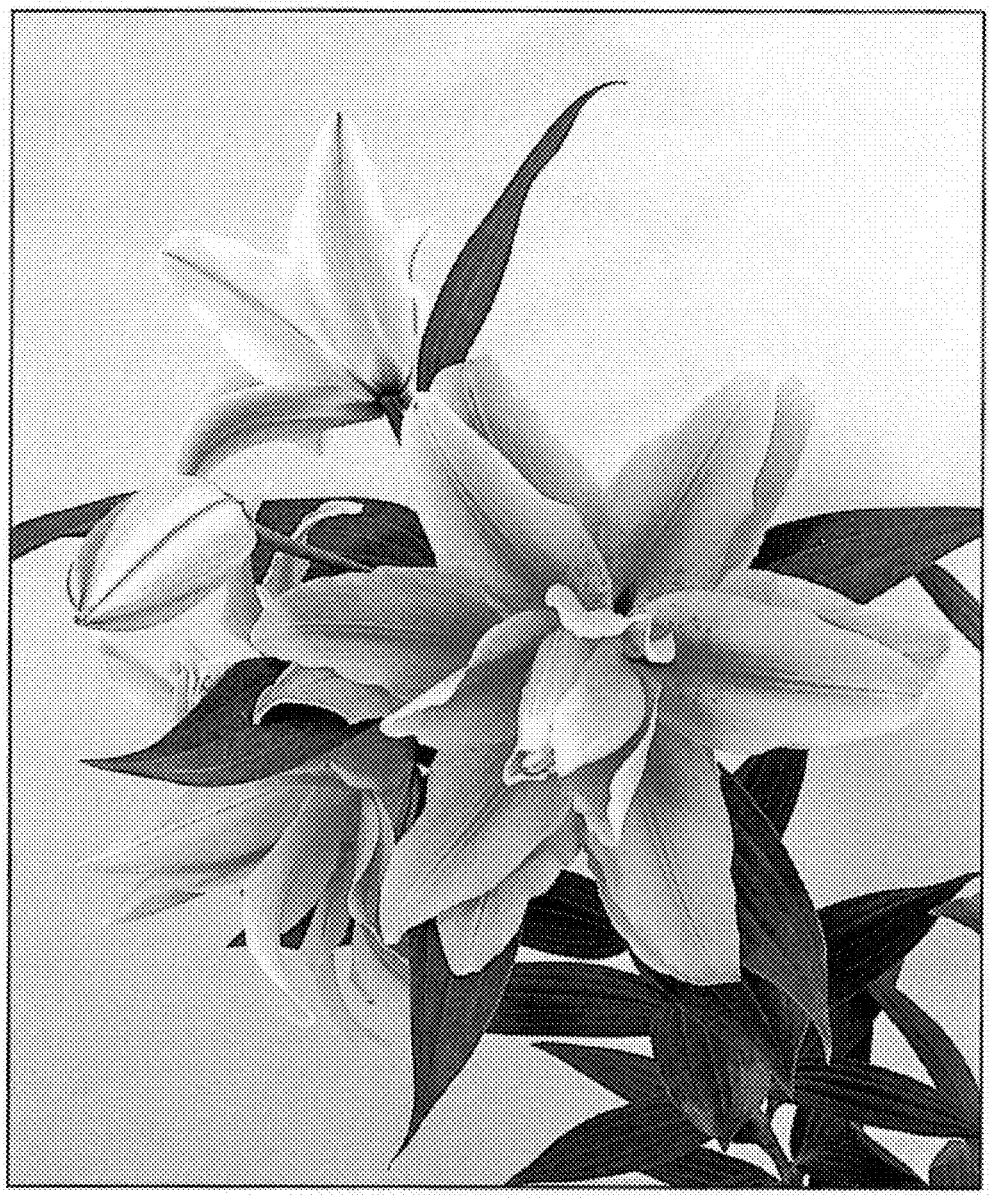
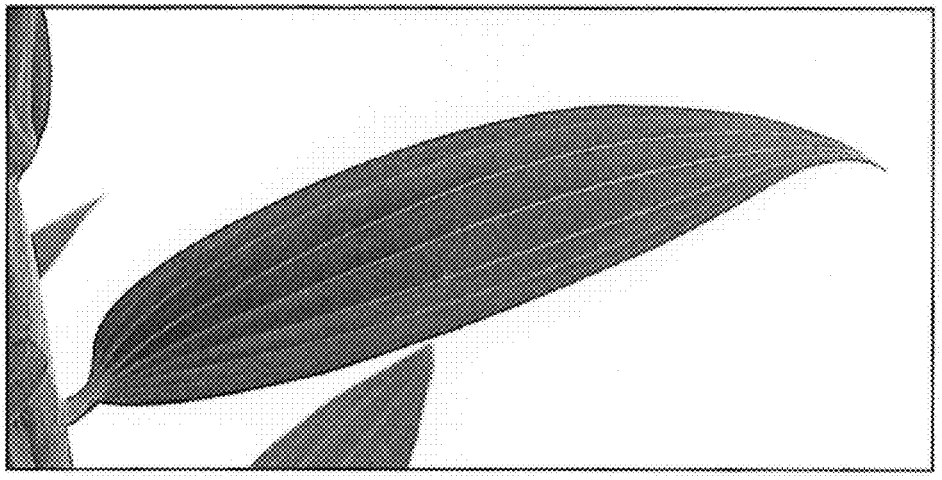

* * * * *